United States Patent [19]

Wong

[11] Patent Number: 5,536,838
[45] Date of Patent: Jul. 16, 1996

[54] METHOD OF SYNTHESIS OF CHROMIUM AMINO ACID NICOTINATE COMPLEX

[75] Inventor: Yeni Wong, Potomac, Md.

[73] Assignee: ConreLabs, Washington, D.C.

[21] Appl. No.: 314,263

[22] Filed: Sep. 30, 1994

[51] Int. Cl.$^6$ ............................. A61K 31/555; C07D 213/80
[52] U.S. Cl. ............................................. 546/5
[58] Field of Search ........................................ 546/5

[56] References Cited

U.S. PATENT DOCUMENTS

| | | | |
|---|---|---|---|
| 4,343,905 | 8/1992 | Szalay | 435/256 |
| 5,108,610 | 4/1992 | King | 514/504 |
| 5,194,615 | 3/1993 | Jensen | 546/5 |

*Primary Examiner*—Mark L. Berch
*Attorney, Agent, or Firm*—Jacobson, Price, Holman & Stern

[57] ABSTRACT

A novel synthesis of a chromium amino acid nicotinate complex which has glucose tolerance factor activity in which nicotinic acid is dissolved in an aqueous solvent, glycine, glutamic acid and cystine are added, chromium chloride is added and, after completion of the reaction, the pH is adjusted with a base and the reaction mixture freeze dried.

13 Claims, No Drawings

METHOD OF SYNTHESIS OF CHROMIUM AMINO ACID NICOTINATE COMPLEX

BACKGROUND OF THE INVENTION

1. Field of the Invention

The present invention relates to the synthesis of a chromium amino acid nicotinate complex which has glucose tolerance factor activity.

2. Description of the Related Art

In addition to being part of several enzyme systems, chromium is associated with a low-molecular weight organic complex termed glucose tolerance factor (GTF) that acts with insulin in promoting normal glucose utilization. Brewer's yeast, which is rich in GTF, has been shown to improve glucose tolerance, lower serum cholesterol and triglycerides in some elderly subjects, and to reduce insulin requirements in some diabetics. Glucose tolerance is usually impaired in protein-calorie malnutrition and some cases have shown a dramatic response to trivalent chromium.

Purified extract from Brewer's yeast containing chromium, nicotinic acid, glycine, glutamic acid and cystine has been shown to have GTF activity (Toepfer, et al, "Chromium Foods in Relation to Biological Activity", *J. Agric. Food Chem*, Vol 21, p. 69, 1973). A synthesis procedure to prepare complexes with a similar composition having GTF activity also has been reported (Toepfer, et al, "Preparation of Chromium-Containing Material of Glucose Tolerance Factor Activity from Brewer's Yeast Extracts and by Synthesis", *J. Agric Food Chem.*, Vol 25, p. 162, 1977).

In this synthesis procedure, chromium complexes were prepared by dissolving 4 grams of $Cr(Ac)_3H_2O$ in 750 milliliters of 80% alcohol containing 2 milliliters of glacial acetic acid that was neutralized with $NH_4OH$ to pH 7. Four (4) grams of nicotinic acid (molar equivalent 2:1 Cr) was added to the contents of the flask and was stirred during refluxing for 3 hours until a distinct color change occurred. Successively, 2.4 grams of glycine (2:1 Cr), 2.4 grams of L-glutamic acid (1:1 Cr), and 2.5 grams of L-cysteine-HCl (1:1 Cr) were added during 4 hours of continuous stirring and refluxing. The material was stirred overnight without being heated. Alcohol was removed in vacuo, the solution was filtered to remove suspended insoluble material, the residue was washed with water, and filtrate and washings were combined and reduced in vacuo to 300 milliliters. This solution of crude material was a deep red color at pH 4.3. This solution was then subjected to purification (see Toepfer, et al (1977) at p. 163).

SUMMARY OF THE INVENTION

Accordingly, it is an object of the present invention to provide a method for the synthesis of a chromium amino acid nicotinate complex which has GTF activity.

It is another object of the present invention to provide a method for the synthesis of a chromium amino acid nicotinate complex which is simple and straightforward.

It is yet another object of the present invention to provide a method for the synthesis of a chromium amino acid nicotinate complex which produces the complex in large quantities without possibility of contamination.

It is a further object of the present invention to provide a method for the synthesis of a chromium amino acid nicotinate complex which does not require a purification step.

These and other objects and advantages of the present invention are achieved by a method in which nicotinic acid is dissolved in an aqueous solvent at a temperature between room temperature and 100° C. and then amino acids are added to the aqueous solvent. The amino acids are glycine, glutamic acid and cystine. After all of the amino acids are dissolved in the aqueous solvent, trivalent chromium salt is added to the aqueous solvent. After a period of time to ensure completion of the reaction, the pH of the reaction mixture is adjusted to about 3 to 6 with a base.

DESCRIPTION OF THE PREFERRED EMBODIMENT

The first step in the synthesis method comprises dissolving nicotinic acid in an aqueous solvent, typically distilled water. The solvent is preferably constantly stirred manually or mechanically, such as with a magnetic bar, to ensure the nicotinic acid is completely dissolved. The aqueous solvent is maintained at a temperature between about room temperature and 100° C. The preferred temperature is about 70° to 85° C., with the most preferred temperature being about 80° C. Generally speaking, the temperature should be controlled so as to avoid any precipitation during the reaction sequence.

The amino acids are then added to the aqueous solvent, preferably with constant stirring. The amino acids used in accordance with the present invention are glycine, glutamic acid and cystine. Preferably, about 1 mole of each of the amino acids is added to the aqueous solvent for every 2 moles of nicotinic acid.

The trivalent chromium salt is added to the aqueous solvent after all the amino acids are dissolved. The trivalent chromium salt is chromium chloride ($CrCl_3$). The trivalent chromium salt is preferably slowly added to the reactor that contains the amino acids mixture. Typically, the trivalent chromium salt is added to the reactor over a period of about 10 to 15 minutes.

The mixture may be allowed to react for an additional 15 minutes to 1 hour, typically about 30 minutes, to ensure the completion of the reaction.

Finally, the pH of the reaction mixture is adjusted to about 3 to 6, preferably about 4.5 to 5.5, and most preferably about 5, with a base. The preferred base is ammonium hydroxide ($NH_4OH$).

The reaction product may be freeze dried in conventional manner. Typical methods of affecting the freeze drying include the use of liquid nitrogen or dry ice.

The chromium amino acid nicotinate complex produced in accordance with the novel synthesis of the present invention may be administered to mammals for veterinary use in animals or for clinical use in humans in a manner similar to other therapeutic agents of this type. In general, the dosage required for therapeutic efficacy will range from about 200 to 400 µg per day.

Typically, the compositions are prepared for oral administration. The compositions may take the form of, for example, capsules and include, as necessary, excipients normally used in oral formulations.

The invention will be better understood by reference to the following illustrative example.

EXAMPLE

Two molar (1.2 g) of nicotinic acid was dissolved in forty times its volume (about 40 ml) in distilled water in a reactor heated at 80° C. with constant stirring. Then one molar of glycine (0.38 g), glutamic acid (0.74 g) and cystine (0.9 g) were added with constant stirring. After all the amino acids were dissolved, one molar (1.35 g) of chromium chloride ($CrCl_3$) was slowly added (0.1 gm/min.) to the reactor that contained the amino acids mixture. The mixture turned a reddish purple and slowly became darker. The mixture was heated for another 30 minutes to ensure the completion of the reaction. Finally, the pH was adjusted to 5 with concentrated $NH_4OH$ and the solution was then freeze dried.

Although the foregoing example illustrates a specific method for the synthesis of a chromium amino acid nicotinate complex, it will be appreciated that the present invention encompasses other methods as more broadly defined above. Accordingly, the present invention should be limited only by the scope of the appended claims.

I claim:

1. A method of synthesizing a chromium amino acid nicotinate complex, comprising dissolving nicotinic acid in an aqueous solvent maintained at a temperature between about room temperature and 100° C., dissolving amino acids in the aqueous solvent containing the dissolved nicotinic acid, the amino acids being glycine, glutamic acid and cystine, adding trivalent chromium salt to the aqueous solvent containing the dissolved nicotinic acid and amino acids, after the reaction is complete adjusting the pH of the reaction mixture to about 3 to 6 with a base, and recovering the complex.

2. The method of claim 1 in which the temperature is maintained between about 70° and 85° C.

3. The method of claim 1 in which the temperature is maintained at about 80° C.

4. The method of claim 1 in which the aqueous solvent is distilled water.

5. The method of claim 1 in which the aqueous solvent is constantly stirred.

6. The method of claim 1 in which the molar ratio of the nicotinic acid to the amino acids and the trivalent chromium salt is 2:1.

7. The method of claim 1 in which the pH is adjusted to about 4.5 to 5.5.

8. The method of claim 1 in which the pH is adjusted to about 5.

9. The method of claim 1 in which the base is ammonium hydroxide.

10. The method of claim 1 in which the reaction mixture is freeze dried.

11. A method of the synthesis of a chromium amino acid nicotinate complex, comprising dissolving about 2 molar nicotinic acid in water at about 80° C. with constant stirring, adding about 1 molar of glycine, glutamic acid and cystine with constant stirring until all of the amino acids are dissolved, adding about 1 molar chromium chloride, heating the mixture for about an additional 15 minutes to 1 hour, adjusting the pH of the mixture to about 5 with concentrated ammonium hydroxide, and recovering the complex.

12. The method of claim 11 in which the chromium chloride is added at the rate of about 0.1 gm/min.

13. The method of claim 11 in which the reaction mixture is freeze dried.

* * * * *